(12) United States Patent
Salimbeni et al.

(10) Patent No.: US 6,864,366 B2
(45) Date of Patent: Mar. 8, 2005

(54) PROCESS FOR THE PREPARATION OF (E)-5-(2-BROMOVINYL)-2'-DEOXYURIDINE

(75) Inventors: Aldo Salimbeni, Lomagna (IT); Carlo Alberto Maggi, Pomezia (IT); Stefano Manzini, Pomezia (IT); Damiano Turozzi, Pomezia (IT)

(73) Assignees: Menarini Richerche S.p.A., Pomezia (IT); Berlin-Chemie AG, Berlin (DE)

( * ) Notice: Subject to any disclaimer, the term of this patent is extended or adjusted under 35 U.S.C. 154(b) by 0 days.

(21) Appl. No.: 10/468,901

(22) PCT Filed: Feb. 21, 2002

(86) PCT No.: PCT/EP02/01833

§ 371 (c)(1),
(2), (4) Date: Aug. 26, 2003

(87) PCT Pub. No.: WO02/068443

PCT Pub. Date: Sep. 6, 2002

(65) Prior Publication Data

US 2004/0077586 A1 Apr. 22, 2004

(30) Foreign Application Priority Data

Feb. 28, 2001 (DE) .......................... 101 09 657

(51) Int. Cl.$^7$ ...................... C07H 19/073; C07H 19/06; A61K 31/7072
(52) U.S. Cl. ................ 536/28.54; 536/28.53; 536/28.4
(58) Field of Search .......... 536/28.54, 28.53, 536/28.4, 28.5; 514/50

(56) References Cited

U.S. PATENT DOCUMENTS 5,220,062 A * 6/1993 Meyer et al. ............. 564/90

FOREIGN PATENT DOCUMENTS

| DE | 29 15 254 | | 11/1979 |
| GB | 215399 | | 5/1924 |
| GB | 2 125 399 | * | 3/1984 |

OTHER PUBLICATIONS

Wyatt P.G. et al.: "A Short High Yielding Synthesis of the Potent ANIT–VZV Carbocyclic Nucleoside Analogue Carb-a–BVDU", Nucleosides & Nucleotides, vol. 14, 1995, pp. 2039–2049, XP002203038, the whole document; in particular: p. 2042, second paragraph.

Westwood, N.B. et al.: "Synthesis and Biological Properties of a New Series of 5–Substituted–Pyrimidine–1–Nucleoside Analogues" Thetrahedron, vol. 54, 1998, pp. 13391–13404, XP002203039, the whole document, in particular p. 13395, scheme 3, step (c).

Ashwell M et al.: "The Synthesis and Antiviral Properties of (E)–5–(2–Bromovinyl)–2'–Deoxyuridine–Related Compounds" Terahedron, vol. 43, no. 20, 1987, pp. 4601–4608, XP002203040, the whole document.

* cited by examiner

*Primary Examiner*—James O. Wilson
*Assistant Examiner*—Michael C. Henry
(74) *Attorney, Agent, or Firm*—Young & Thompson

(57) ABSTRACT

Process of preparing (E)-5-(2-bromovynyl)-2'-deoxyuridine (Brivudine) characterized in that halogen-free solvent selected form esters or cyclic ethers are used in the bromination step of 5-ethyl-2'-deoxyuridine diacylate. The use of solvents is advantageous in respect of toxicity, discharge costs and environment protection.

14 Claims, No Drawings

PROCESS FOR THE PREPARATION OF (E)-5-(2-BROMOVINYL)-2'-DEOXYURIDINE

The present invention discloses a process for the preparation of (E)-5-(2-bromovinyl)-2'-deoxyuridine (Brivudine) wherein halogen-free solvents are used in the whole process and in particular in the first step of bromination of 5-ethlyl-2'-deoxyuridine diacylate.

STATE OF THE ART (E)-5-(2-bromovinyl)-2'-deoxyuridine (Brivudine) of formula I is a compound endowed with strong antiviral activity, particularly useful for the treatment of Herpes Zoster infections.

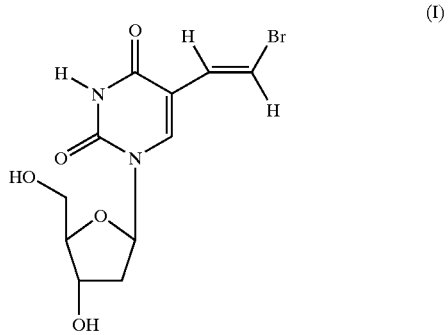

(I)

A first method of synthesis is described in DE 2 915 254 and comprises the alkylation of (E)-5-(2-bromovinyl)uracile with 1-chloro-2-deoxy-3,5-di-O-p-tolyl-α-D-erithro-pentafuranose and subsequent deacylation to give the compound of formula I.

A drawback of this method is that the synthesis of (E)-5-(2-bromovinyl)uracile is troublesome and gives poor yields. Moreover, the compound of formula I obtained thereby is not pure, but is a mixture of alpha and beta isomers. Only the latter has a practical value and needs to be isolated by chromatographic separation.

An alternative method is described in GB 2 125 399 (corresponding DE 33 28 238) and comprises the bromination of compounds of formula II

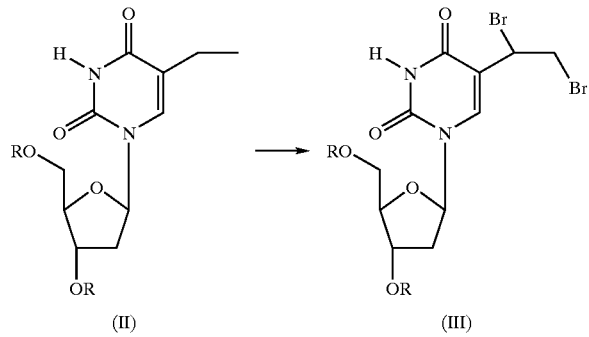

(wherein R is an alkanoyl C1–C8 group, a benzoyl group or a benzoyl group substituted at the para position with a C1–C4 alkyl group or with a halogen atom) with bromine in a halogenated hydrocarbon solvent (such as, 1,2-dichloroethane, methylene chloride, chloroform, carbon tetrachloride), in the presence of light, to give the dibromo-derivative of formula III (wherein R is defined as above). Said compound III is then dehydrobrominated in a halogenated hydrocarbon solvent, in the presence of a tertiary base, to give the nucleoside of formula IV (wherein R has the same meanings indicated for the compounds of formula II),

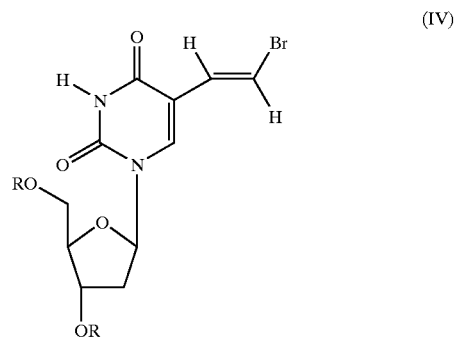

(IV)

with a yield of 62–69%: after removal of the protective groups, (E)-5-(2-bromovinyl)-2'-deoxyuridine of formula I is obtained with a yield of about 93%.

Over the last years bromrochloromethane has become in the industrial practice the solvent of choice in radical reactions promoted by thermal initiators, due to its relatively high boiling point (68° C.) and to its lower toxicity compared with other halogenated solvents such as, for example, chloroform, carbon tetrachloride, 1,2-dichloroethane. Nevertheless, the use of this solvent has been recently forbidden because of the risks connected to the reduction of the ozone layer (see CEE regulation N.2037/2000 of the European Parliament).

DISCLOSURE OF THE INVENTION

It has now been found that Brivudine can be advantageously obtained by reaction of the compounds of formula II and III as defined above in a solvent selected from alkyl esters or cyclic ethers.

The use of said halogen-free solvents is advantageous compared with the use of halogenated solvents, since the former have a lower toxicity, comply with the European provisions concerning environment protection and allow to diminish of about 50% the industrial discharge costs.

The invention provides therefore a process comprising:

a) radicalic bromination of compounds of formula II (in which R is as defined above) by means of a brominating agent in a halogen-free solvent selected from alkyl esters and cyclic ethers, in the presence of a radical initiator, to give compounds of formula (III), in which R has the above meaning;

b) dehydrobromination in a halogen-free solvent, with or without bases, to obtain the compounds of formula IV, in which R has the above meaning;

c) deprotection to obtain the compound of formula (I).

A preferred R group is para-chloro-benzoyl.

The brominating agent, which can be bromine or N-bromosuccinimide, N-bromo phtalimide, 1,3-dibromo-5, 5-dimethylidantoine, N-bromoacetamide, N-bromomaleimide, N-bromosulfonamide, is used in a molar excess ranging from 2 to 3 times compared with compound II. Bromine e N-bromosuccinimide are particularly preferred.

Examples of halogen-free solvents for step a) comprise alkyl acetates such as methyl, ethyl, n-propyl, isopropyl, n-butyl, isobutyl acetate or a cyclic aliphatic ether such as 1,4-dioxane, preferably in a ratio ranging, from 3:1 to 12:1 compared with compound II. Ethyl acetate and 1,4-dioxane are particularly preferred.

The solvent used for dehydrobromination (step b) is dimethylformamide or dimethylacetamide or can be the same as that used in the bromination step. Ethyl acetate and N,N-dimethylformamide are particularly preferred.

2,2'-Azobisisobutyronitrile (AIBN), 2,2'-azobis(2,4-dimethylvaleronitrile), 2,2'-azobis(2-methylbutyronitlile), azobisisovaleronitrile, 1,1'-azobis-(cyclohexancarbonitrile), 2,2'-azobis(2-amidinopropane) hydrochloride, dimethyl 2,2'-azobisisobutirrate can be used as radical initiators. Azobisisonitriles are preferred, in particular AIBN.

Said compounds are used in molar percentages ranging from 1 to 6% (3 and 6% for AIBN), compared with compound II.

The reaction temperature ranges from room temperature to the boiling point of the solvent and the reaction time ranges from 15 minutes to 4 hours. Preferred conditions comprise the reaction with N-bromosuccinimide in the presence of 2,2'-azobisisobutyronitrile. (AIBN) in ethyl acetate at the boiling temperature of the solvent or the reaction with N-bromosuccinimide in the presence of AIBN in 1,4 dioxane at a temperature ranging from 70 to 90° C.

Further to the economic advantages deriving from the lower discharge costs, the lower toxicity and the compliance with the regulations concerning environment protection, as above discussed, the process of the invention is also characterized by particularly high yields. This is particularly surprising, since it is known from chemical literature that the majority of the radicalic bromination reactions is usually carried out in halogenated solvents: for example, the already cited GB 2 125 399 describes only the use of chlorinated solvents for the synthesis of Brivudine, in accordance with the common general knowledge available in this technical field.

Moreover, not all of the halogen-free solvents can be advantageously used in the process of synthesis and only some of them provide satisfactory results.

For example, in the process for the preparation of Brivudine described in DE 2 915 254, the bromination of (E)-5-vinyl-uracile occurs in anhydrous dimethylformamide. Nevertheless, when dimethylformamide is used in the present process in the bromination step of the compounds of formula II, the conversion yields are surprisingly low and a number of not precisely identified by-products are formed. Another halogen free solvent sometimes used in radical brominations is acetonitrile (J.A.C.S. 1969 (91) 7398–740; J.A.C.S. 1971 (93) 5846–5850; J.A.C.S. 1974 (96) 5616–5617), but also this solvent has not given satisfactory results in the bromination of compounds of formula II. Equally unacceptable results are obtained also with ether-like solvents such as 1,2-dimethoxyethane o methylcellosolve.

The process according to the invention is further illustrated in the following examples.

The starting intermediates of formula II (wherein R is as defined above) are prepared with a known method, as reported in GB 2 125 399.

EXAMPLE 1

10.0 g (18.7 mmol) of 3',5'-di-O-p-chlorobenzoyl-5-ethyl-2'-β-deoxyuridine of formula II wherein R=4-ClC$_6$H$_4$CO and 175 mg (1.1 mmol) of α,α'-azoisobutyronitrile (AIBN) are added to 60 ml of ethyl acetate and the mixture is refluxed.

2.05 ml (6.33 g; 39.6 mmol) of bromine in 8 ml of ethyl acetate are dropped into the mixture depending on the consumption of the halogenating agent (discolouration of the mixture can be observed). The solution obtained at the end of the addition is heated for further 15 minutes until the reflux becomes colourless. The solvent is evaporated under reduced pressure.

The residue consisting of the dibromoderivative of formula III wherein R=4-ClC$_6$H$_4$CO is dehydrobrominated similarly to what described in GB 2125399 using DMF as the solvent.

8.0 g of 3',5'-di-O-p-chlorobenzoyl-(E)-5-(2-bromovinyl)-2'-β-deoxyuridine of formula IV wherein R=4-ClC$_6$H$_4$CO are obtained (yield: 70%) which are then deacylated with a known method, for example as reported GB 2 125 399. 4.1 g of (E)-5-(2-bromovinyl)-2'-β-deoxyuridine of formula I are obtained (yield: 94%).

EXAMPLE 2

10.0 g (18.7 mmol) of 3',5'-di-O-p-chlorobenzoyl-5-ethyl-2'-β-deoxyuridine of formula II wherein R=4-ClC$_6$H$_4$CO and 175 mg (1.1 mmol) of α,α'-azoisobutyronitrile (AIBN) are added to 60 ml of ethyl acetate and refluxed.

7.85 g (44.1 mmol) of N-bromosuccinimide are added to the mixture in accordance with the reaction rate (about 25 minutes). At the end of the addition the mixture is heated for further 15 minutes until it becomes clear. The residue consisting of the dibromoderivative of formula III, wherein R=4-ClC$_6$H$_4$CO, is dissolved in 60 ml of hot AcOEt and 3.3 ml (23.6 mmol) of triethylamine are dropped into the solution. The precipitate is filtered and treated with 80% EtOH. The undissolved material, consisting of the compound of formula IV wherein R=4-ClC$_6$H$_4$CO, is filtered, washed with EtOH and dried under reduced pressure. 9.4 g of the compound of formula IV wherein R=4-ClC$_6$H$_4$CO are obtained (yield: 82%) and are then deacylated with a known method, for example as reported in GB 2 125 399. 4.8 g of the compound of formula I are obtained (yield: 94%).

EXAMPLE 3

The bromination is carried out according to example 1 at 80° C. using isobutyl acetate as the solvent.

The addition of the bromine solution in isobutyl acetate is carried out within 20 minutes. At the end of the addition) the solution is heated for further 15 minutes until it becomes colourless, thereafter the reaction is carried out as described in example 2. 8.6 g of the compound of formula IV wherein R=4-ClC$_6$H$_4$CO are obtained (yield: 75%) and are then deacylated with a known method, for example as reported in GB 2 125 399. 4.4 g (yield: 94%) of the compound of formula I are obtained (yield: 94%).

EXAMPLE 4

The bromination is carried out according to example 2 at 80° C. using isobutyl acetate as the solvent.

Continuing to follow the procedure reported in example 2, 9.0 g of the compound of formula IV in which R=4-ClC$_6$H$_4$CO are obtained (yield: 79%) and are then deacylated with a known method, for example as reported in GB 2 125 399. 4.6 g of the compound of formula I are obtained (yield: 94%).

EXAMPLE 5

10.0 g (18.7 mmol) of 3',5'-di-O-p-chlorobenzoyl-5-ethyl-2'-deoxyuridine of formula II wherein R=4-ClC$_6$H$_4$CO and 175 mg (1.1 mmol) of α,α'-azoisobutyronitrile (AIBN) are added to 25 ml of 1,4-dioxane. The mixture is heated at 80° C. and then a solution of 8.5 g (47.7 mmol) of N-bromosuccinimide in 35 ml of 1,4-dioxane is dropped in accordance with the reaction rate (about 30 minutes). After completion of the addition the solution is heated for further 15 minutes until it becomes colourless. The reaction is continued as described in example 1; 8.8 g of the compound of formula IV wherein R=4-ClC$_6$H$_4$CO are obtained (yield: 77%) and are then deacylated with a known method, for example as reported in GB 2 125 399. 4.5 g of the compound of formula I are obtained (yield: 94%).

EXAMPLE 6

Following the procedure described in example 2 and using ethyl acetate as the solvent and 1,1'-bis (cyclohexancarbonitrile) (270 mg, 1.1 mmol) as the radical initiator, 8.1 g (71%) of the compound of formula IV wherein R=4-ClC$_6$H$_4$CO are obtained and are then deacylated with a known method, for example as reported in GB 1 125 399. 4.2 g of the compound of formula I are obtained (yield: 95%).

What is claimed is:

1. Process for the preparation of (E)-5-(2-bromovinyl)-2'-β-deoxyuridine of formula I

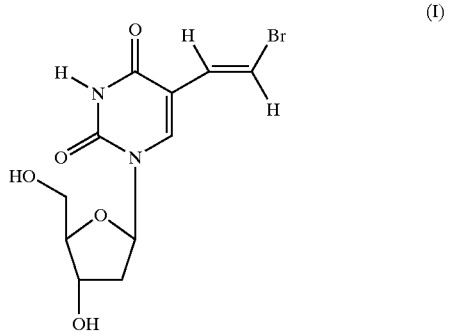

(I)

comprising:

a) reaction of a compound of formula II,

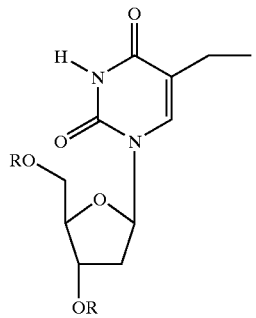

(II)

in which R is an alkanoyl C1–C8 group, a benzoyl group or a benzoyl group substituted at the para position with a C1–C4 alkyl group or with a halogen atom, with a brominating agent in the presence of a radical initiator, in a halogen-free solvent selected from an alkyl ester or a cyclic ether;

b) dehydrobromination of the resulting compound of formula (III)

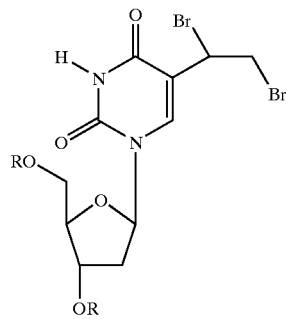

(III)

wherein R has the above defined meaning, with or without bases, in a halogen-free solvent to give an intermediate of formula (IV),

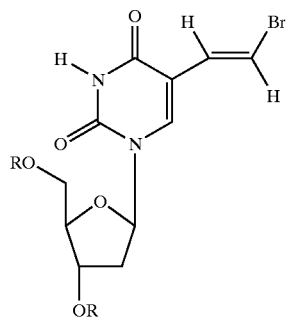

(IV)

wherein R has the above defined meaning;

c) deprotection of the intermediate of formula (IV).

2. Process as claimed in claim 1, in which the reaction of bromination in the step a) is carried out in a halogen-free solvent selected from the group consisting of methyl, ethyl, n-propyl, isopropyl, n-butyl, isobutyl acetate, 1,4-dioxane.

3. Process as claimed in claim 1 which comprises the reaction of a compound of formula II wherein R is a group 4-C1C6H$_4$CO.

4. Process as claimed in claim 1 wherein the reaction is carried out with molecular bromine in the presence of a radical initiator.

5. Process as claimed in claim 1 wherein the reaction is carried out with N-bromosucciminide in the presence of a radical initiator.

6. Process as claimed in claim 1 wherein the reaction is carried out with N-bromosuccinimide in the presence of 2,2'-azobisisobutyronitrile (AIBN) in ethyl acetate at the boiling temperature of the solvent.

7. Process as claimed in claim 1 wherein the reaction is carried out with N-bromosuccinimide in the presence of AIBN in 1,4 dioxane the temperature ranging from 70 to 90° C.

8. Process as claimed in claim 1 in which the dehydrobromination in step b) is carried out in ethyl acetate or N,N-dimethylformamide or N,N-dimethylacetamide.

9. Process as claimed in claim 2 which comprises the reaction of a compound of formula II wherein R is a group 4-ClC6H$_4$CO.

10. Process as claimed in claim 2 wherein the reaction is carried out with molecular bromine in the presence of a radical initiator.

11. Process as claimed in claim 2 wherein the reaction is carried out with N-bromosucciminide in the presence of a radical initiator.

12. Process as claimed in claim 2 wherein the reaction is carried out with N-bromosuccinimide in the presence of 2,2'-azobisisobutyronitrile (AIBN) in ethyl acetate at the boiling temperature of the solvent.

13. Process as claimed in claim 2 wherein the reaction is carried out with N-bromosuccinimide in the presence of AIBN in 1,4 dioxane the temperature ranging from 70 to 90° C.

14. Process as claimed in claim 2 in which the dehydrobromination in step b) is carried out in ethyl acetate or N,N-dimethylformamide or N,N-dimethylacetamide.

* * * * *